United States Patent [19]

Primiano

[11] Patent Number: 5,027,798

[45] Date of Patent: Jul. 2, 1991

[54] WATER JET TEETH FLOSSING APPARATUS

[76] Inventor: Michael J. Primiano, Lake Oswego, Oreg.

[21] Appl. No.: 231,495

[22] Filed: Aug. 10, 1988

[51] Int. Cl.⁵ .............................................. A61H 9/00
[52] U.S. Cl. .................................................... 128/66
[58] Field of Search ................ 128/62 A, 66; 433/80; 604/77, 150; 4/606, 605, 615, 597

[56] References Cited

U.S. PATENT DOCUMENTS

| | | | |
|---|---|---|---|
| 2,733,713 | 2/1956 | Kabnick | 128/62 A |
| 3,593,707 | 2/1971 | Pifer | 128/62 A |
| 3,771,517 | 11/1973 | Radecki | 128/62 A |
| 4,265,229 | 5/1981 | Rice et al. | 128/66 |
| 4,564,005 | 1/1986 | Marchand et al. | 128/66 |
| 4,793,331 | 12/1988 | Stewart | 128/66 |
| 4,807,604 | 2/1989 | Canela | 128/66 |
| 4,808,109 | 2/1989 | Thornton | 128/66 |
| 4,862,021 | 9/1989 | Siderman | 128/66 |

Primary Examiner—Cary E. Stone
Attorney, Agent, or Firm—Olson & Olson

[57] ABSTRACT

A dental water jet flossing apparatus comprises an elongated, flexible tubing attached at one of its ends directly to a household water supply, preferably at a point where water temperature can be controlled, as at the water outlet pipe mounting a shower head. The opposite end of the tubing is connected to a hand-held unit that is configured to releasably mount a dental water jet nozzle. A water flow control valve is included in the hand unit and configured to engage the flexible tubing and selectively constrict the latter to various desired degrees to selectively control the amount and rate of water delivered through the tubing and hence expelled from the nozzle. A syphon cup containing mouthwash or the like may be provided in-line to meter desired fluids into the water being delivered out of the nozzle and into the user's mouth.

2 Claims, 2 Drawing Sheets

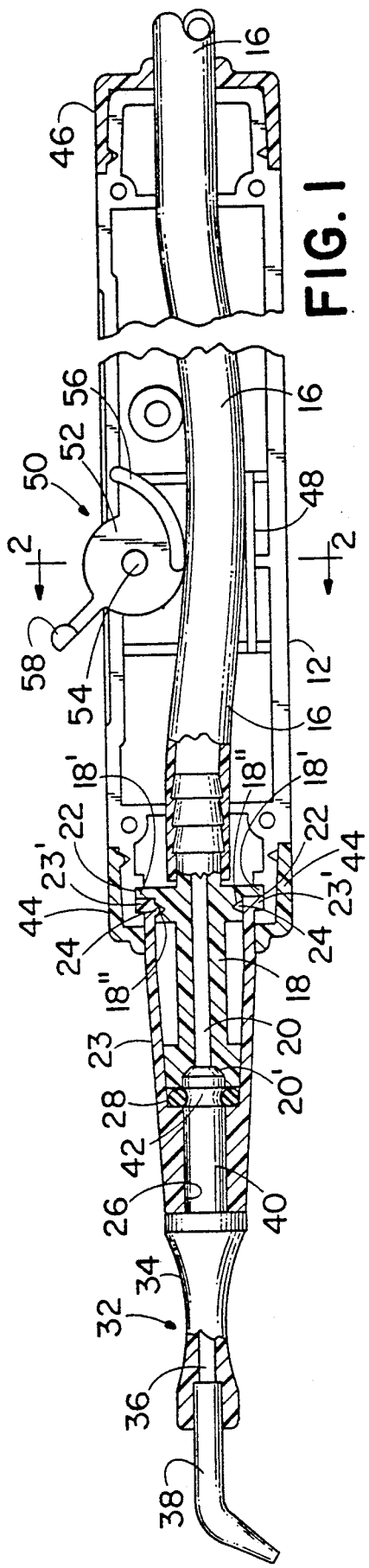
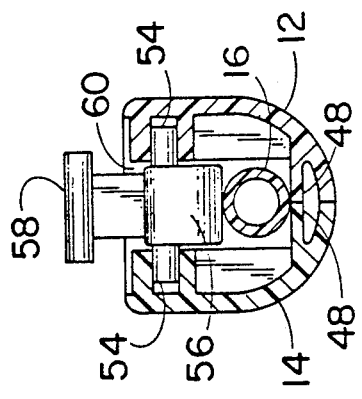

1

WATER JET TEETH FLOSSING APPARATUS

BACKGROUND OF THE INVENTION

This invention relates to water jet teeth flossing devices, and more particularly to a water jet flossing apparatus configured to be attached to a conventional water supply, as for example a sink faucet or shower head fixture, for flossing one's teeth using only the conventional water system in a house for an adequate suppy of water under pressure.

Water jet flossing devices are well known in the art. Generally, such devices comprise a hand held unit which mounts a removable water jet nozzle that is manipulated around the teeth to inject pulses of water under pressure between the teeth and at the gum line. The hand unit is connected by an elongated flexible tube to a base unit, usually disposed on a counter, the base unit having a water pump which communicates with a water reservoir contained in the base unit. Typically, warm water is placed into the reservoir, sometimes with mouthwash or other dental antiseptics added, and the pump activated to expel the contents of the reservoir out through the tubing to the hand unit. A regulator is usually provided in the base unit to selectively control the pump, and hence the amount and velocity of the water expelled through the nozzle into the mouth.

These devices are usually fairly expensive since they require not only their own water reservoir, but also a pump, motor, electronics and the labor required to assemble the materials into working devices. Moreover, since they do employ a number of moving, mechanical parts, they are also subject to wear through continued use, and ultimate failure. Additionally, since the units must be filled with water prior to use, and access to a sink to dispose of water expelled into the mouth is needed during use, their placement near a water supply and a drain is a requisite to their use.

SUMMARY OF THE INVENTION

In its basic concept, this invention provides a water jet tooth flossing apparatus that comprises basically a hand held nozzle assembly connected through an elongated tubing to the output of a conventional household water line, as at a shower, tub or sink.

It is by virtue of the foregoing basic concept that the principal objective of this invention is achieved; namely the provision of a water jet dental flossing apparatus which overcomes the necessity of utilizing mechanical moving parts, electricity, a water reservoir and a water pump to achieve a water jet action necessary and desirable for adequate flossing of teeth.

Another object of this invention is the provision of a water jet apparatus of the class described which is connected to the water line easily, with no special tools or skills required, and is connected at or near the faucet, so that the water temperature may be easily regulated as desired.

Another object of this invention is the provision of a water jet flossing apparatus of the class described which may be used simultaneously with the operation of a conventional shower without interruption of the shower or noticable disruption of the temperature or water flow of the shower.

Another object of this invention is the provision of a water jet flossing apparatus of the class described which may include an in-line suction-type dispenser for mouthwash, etc. that meters the addition of desired material into the water being delivered to the jet nozzle.

Still another object of this invention is the provision of a water jet apparatus of the class described in which the flow and velocity of the expelled water may be fully controlled a the hand unit.

A further object of this invention is the provision of a water jet flossing apparatus of the class described which is of greatly simplified construction for economical manufacture.

The foregoing and other objects and advantages of this invention will appear from the following detailed description, taken in connection with the accompanying drawings of a preferred embodiment.

BRIEF DESCRIPTION OF THE DRAWINGS

FIG. 1 is a fragmentary foreshortened side elevation of the hand unit of a water jet apparatus embodying the features of this invention, the view taken with the facing side panel removed and the securing end caps shown in section in order to better illustrate internal detail.

FIG. 2 is a sectional view taken along the line 2—2 in FIG. 1, the facing side panel omitted in FIG. 1 being shown herein in proper assembled condition.

DESCRIPTION OF THE PREFERRED EMBODIMENT

Figure 3:
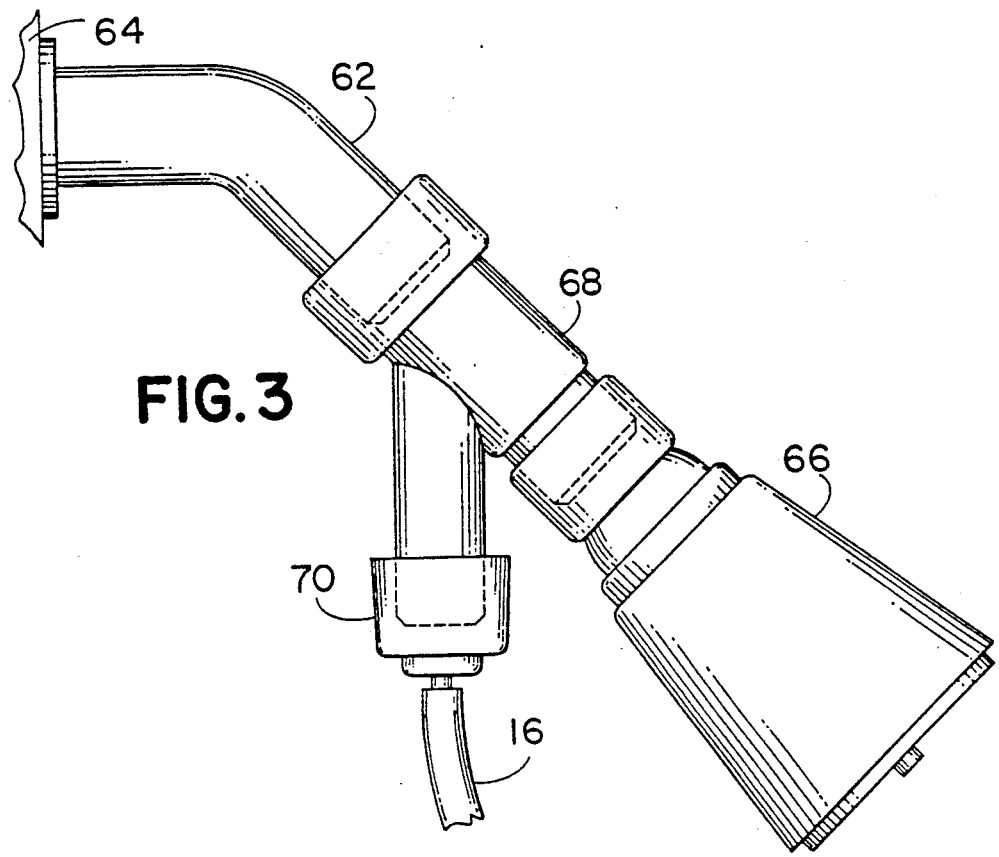
FIG. 3 is a fragmentary side elevation of a conventional shower head arrangement mounting a connector that attaches the hand unit of FIG. 1 to the water supply provided in a shower.

A water jet tooth flossing device comprises a hand unit, illustrated generally as 10, having opposite side half members 12 and 14 that form, when assembled together as in FIG. 2, a substantially hollow cavity. An elongated water delivery tube 16 is carried within the body and passes out the rear end, i.e. to the right in FIG. 1, to a source of water under pressure as will be discussed later.

The tube 16 is connected to a tubing coupler 18 which is mounted to the housing members 12 and 14 adjacent their forward end. The coupler has an internal bore 20 extending through its longitudinal center. In this embodiment, the bore has an enlarged portion 20' adjacent the outer terminal end to the coupler. As illustrated, the housing members 12 and 14 include a circular notch 22 which receives the enlarged end 18' of the coupler 18, the coupler including an annular groove 18" adjacent the enlarged end 18' as illustrated, for purposes which will now be described.

As illustrated in FIG. 1, a hollow sleeve 23 is configured to overlie the coupler 18, the sleeve including an enlarged inner end 23' which is also configured to be captured in the notch 20 provided in the housing body members 12 and 14. When so positioned, an internal, projecting annular ring 24 adjacent the inner end of the sleeve 23 engages the annular groove 18" on the coupler 18 in a snap fit arrangement, thus securely locking them together. The sleeve includes an internal bore 26 aligned with the enlarged section 20' of the bore through the coupler 18.

As shown, an O-ring 28 is interposed between the outer terminal end of the coupler 18 and a confronting surface 30 within the sleeve, thereby forming a water-tight seal between the two pieces to prevent any undesirable leakage of water under pressure around the bores 20' and 26. This O-ring also provides means by which a conventional, removable water jet nozzle piece 32 is secured in position attached to the sleeve.

Conventional nozzle pieces 32 are provided to be easily removable so that each individual may have his own mouthpiece to use, for sanitary reasons. These nozzles typically include a body portion 34 having an internal bore 36 therethrough, a forwardly extending nozzle tip 38, and a rearwardly projecting hollow shaft 40 that fits into the bore 26 in the sleeve 22. An annular groove 42 is provided in the shaft 40 adjacent its end, the groove recceiving the inner circumferential edge of the O-ring 28 in a snug, water-tight snap fit arrangement.

In this embodiment, a pair of front and rear end caps 44, 46 are provided to overlie the ends of the side housing members 12, 14 when assembled, to secure them together in the assembled condition illustrated best in FIG. 2. Alternatively, the housing members 12 and 14 can be secured together by bonding, screws or other desirable, suitable means.

Means is provided to manually control the rate at which water under pressure is delivered out of the nozzle. In this embodiment, control means is provided by a simplified valve arrangement which is arranged to manually constrict the tubing 16 to various degrees within the hand unit housing.

As illustrated near the bottom of FIGS. 1 and 2, a tube-support ledge 48 is Provided within the housing body upon which the tubing 16 is disposed. A control valve 50 is pivotally mounted on the housing body on the side of the tube opposite the ledge 48. The control valve comprises a circular member 52 rotatably mounted within the housing by pivot member 54. The circular member 52 is configured, as shown, with an off-center projecting portion 56 that comprises a circumferential surface segment of a larger circle, arranged so that rotation of the member 52 about the pivot 64 results in the projecting portion 56 effectively pinching off the tubing against the ledge 48. As the member 52 is rotated further, the increasingly more projecting portion 56 constricts the tubing to a greater and greater degree, thereby selectively controlling the flow as desired. A finger lever 58 is provided on the member 52 to extend through a slot 60 in the housing for easier manipulation of the valve 50.

Figure 4:
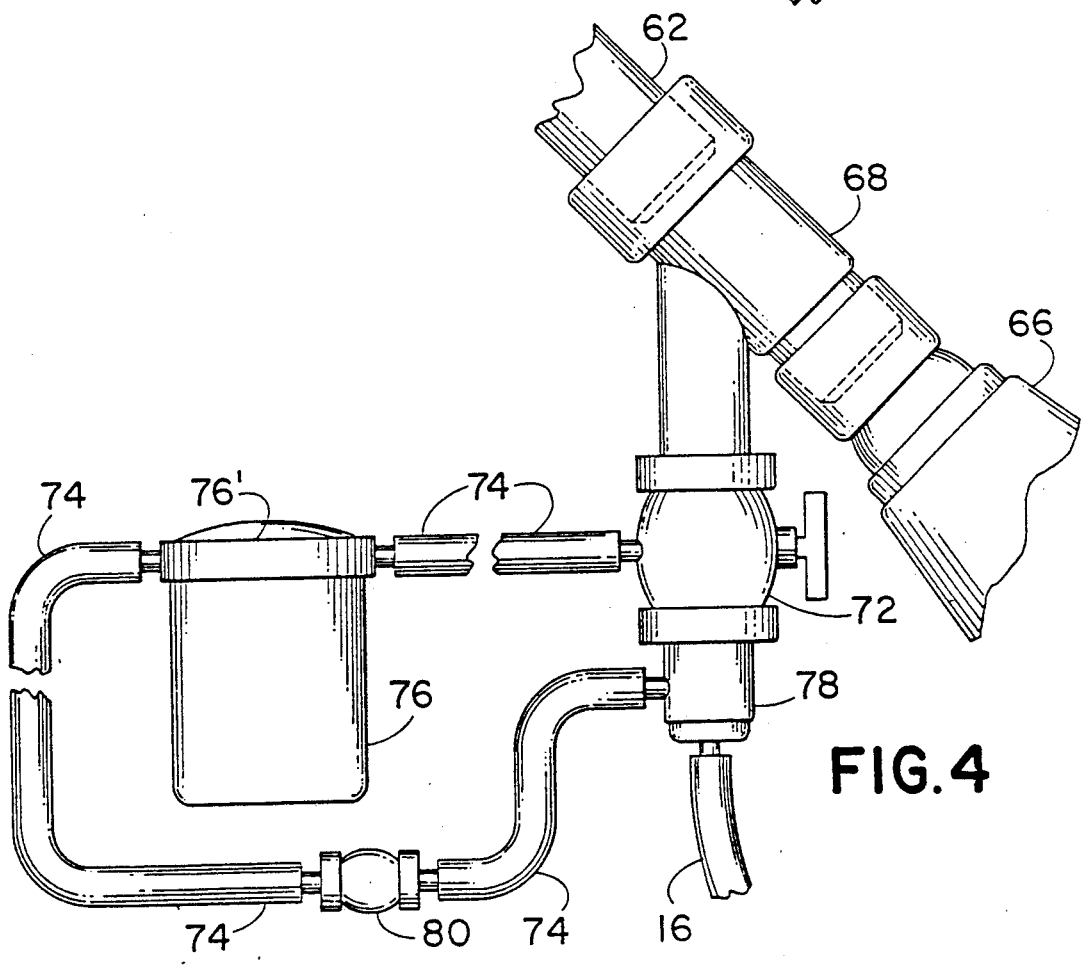
FIG. 4 is a fragmentary, foreshortened schematic view of one embodiment of an in-line attachment apparatus arranged to meter and disPense mouthwash, etc. into the water being delivered to the hand unit.

Referring now to FIGS. 3 and 4, means is provided to connect the elongated tubing 16 extending from the hand unit 10 to a source of water under pressure. A principal object of this invention is to utilize the household water supply, thereby eliminating the cost, inconvenience and mechanics of water reservoirs, pumps, filling, etc. associated with all conventional water jet flossing devices heretofore available in the art. To this end, it is desirable, but not essential that the tubing 16 be connected to a household water suPPly at a point in which the water temperature can be regulated. Therefore, a sink faucet or a shower head outlet is ideal for the purpose.

There is illustrated in FIGS. 3 and 4 a conventional shower pipe 62 extending from a wall 64, and a typical shower head 66. It will be understood however, that conventional hand-held portable shower heads, massage-type shower heads, and other typical fittings are equally applicable, without affecting the use or operation of the invention. This invention provides a "T" coupler 68 simply interposed between the shower pipe 62 and the shower head 66, the T-coupler mounting an adapter fitting 70 to which the tubing is attached, and the water thereby supplied to the hand unit 10 of this invention. Installation simply involves unscrewing the shower head 66 from its supply pipe, screwing the T-connector 68 onto the pipe, and screwing the shower head onto the outlet end of the T-connector, and finally screwing the tube mounting adapter fitting 70 onto the T-connector.

FIG. 4 shows the shower pipe 62, shower head 66 and T-connector 68 of FIG. 3 as described above, but also schematically illustrates an attachment arrangement for adding mouthwash and the like to the water as it is delivered to the hand unit.

Basically, a bypass valve 72 is attached to the T-connector 68 for selectively controlling the flow of water either in a straight line through the valve and into tube 16 or channeled first through a second tube 74. This second tube is connected, in this embodiment, to one side of a conventional syphon cup 76 containing mouthwash. As is conventional, the tube 74 exits the opposite side of the syphon cup and is connected to the main below after the valve 72 at a tube mounting adapter fitting 78, the outfeed end of which mounts the tube 16. In use, water under pressure can flow straight through the valve 72 and directly to the tube 16 connected to the hand unit 10, or, if desired, channeled by valve 72 through the arrangement just described.

In this, the water passes through the syphon cup cap 76' drawing mouthwash contained in the cup into the water supply by a metered venturi action. The water, now containing mouthwash, is returned to the main line at the fitting 78 and thence to the hand unit. A one-way ball check valve 80 is preferably provided in line 74 to prevent backflow. Other arrangements for injecting desired liquids or solids into the water supply in metered fashion may alternatively be provided as needed or desired.

In the operation of the flossing device, when the control valve 50 on the hand unit is opened to allow water to flow from the shower pipe 62 and out the nozzle top 38, the total volume of water expelled is insignificant compared with that of the household water supply. Therefore, operation of the flossing apparatus does not affect the operation of the shower or faucet, and accordingly, the device may be used simultaneously with a shower without diminishing the operation of the shower at all. If desired of course, the shower may also be shut off at the shower head during flossing.

From the foregoing it will be apparent to those skilled in the art that the present invention provides a unique and greatly simplified version of a conventional dental water jet flossing apparatus. The elimination of the traditional base unit normally placed on a counter adjacent a sink has been found to result only in the elimination in the disadvantages and limitations of heretofore available, conventional water jet flossing apparatus found in the art. With no base unit, counter space is freed, and since the prior devices required being located near a water supply and a drain, the present invention's attachment to the household water supply at a sink faucet or shower or tub water fixture, is ideal, and does not pose any new requirement or routine on the user. Moreover, since there is no pump involved, no source of electricity is required, and since no water reservoir is involved, no time or inconvenience in filling and emptying a reservoir is involved either. Additionally, by eliminating mechanical moving parts, and electrical components, wear and subsequent failure is virtually eliminated, and also are the manufacturing expenses associated therewith.

From the foregoing it will also be apparent to those skilled in the art that various changes, other than those already described, may be made in the size, shape, type, number and arrangement of parts described hereinbefore without departing from the spirit of this invention and the scope of the appended claims.

Having thus described my invention and the manner in which it is used,

I claim:

1. A water jet type dental flossing apparatus for connection to a standard household shower head-mounting plumbing fitting, the flossing apparatus comprising:

(a) a plumbing fitting for attachment to a conventional shower supply water line carrying water under pressure to a conventional shower head, the plumbing fitting comprising a "T" fitting having an inlet end and a pair of outlet ends and an unrestricted water passageway communicating said inlet end with said pair of outlet ends, the inlet end configured for attachment to a water supply line for unrestricted flow of water through both of said outlet ends, one outlet end configured to mount a conventional shower head, (b) an elongated, flexible tubing connected at one of its ends to the other outlet end of said plumbing "T" fitting, the tubing configured to carry water under pressure, (c) a water jet nozzle connected to the opposite end of said elongated, flexible tubing, the water jet nozzle configured to supply a stream of water under pressure into a user's mouth about the teeth and gums, and (d) a hand unit comprising an elongated hollow body having front and rear ends, the rear end receiving therethrough the end of the flexible tubing opposite the end connected to the plumbing fitting, a water jet nozzle mounting member secured to the front end of the hollow body and having on its inner end a coupler connecting the end of the flexible tubing contained in the hollow body, the outer end of the mounting member configured to removably mount the water jet nozzle in communication with the flexible tubing, and control pinch valve means on the hollow body engaging the flexible tubing therein and operable to control the flow of water to the water jet nozzle.

2. The dental flossing apparatus of claim 1 wherein the water jet nozzle mounting member includes an elongated coupler member having a longitudinal bore therethrough, the inner end of said coupler member being connected to the flexible tubing, a hollow sleeve member having inner and outer ends and containing the coupler member therein, the inner end of the sleeve member being attached to the front end of the hollow body, the outer end of the sleeve member having a bore communicating with the longitudinal bore in the coupler member and configured to removably mount the water jet nozzle.

* * * * *